US008952064B2

(12) United States Patent
Vanderbist et al.

(10) Patent No.: US 8,952,064 B2
(45) Date of Patent: *Feb. 10, 2015

(54) PHARMACEUTICAL SEMI-SOLID COMPOSITION OF ISOTRETINOIN

(75) Inventors: Francis Vanderbist, Beersel (BE); Cécile Servais, Malonne (BE); Philippe Baudier, Uccle (BE)

(73) Assignee: Galephar Pharmaceutical Research, Inc., Humacao, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/525,857

(22) Filed: Jun. 18, 2012

(65) Prior Publication Data
US 2013/0158119 A1    Jun. 20, 2013

Related U.S. Application Data

(63) Continuation of application No. 11/892,363, filed on Aug. 22, 2007, now Pat. No. 8,367,102, which is a continuation-in-part of application No. 10/380,619, filed as application No. PCT/BE01/00163 on Sep. 21, 2001, now Pat. No. 7,435,427.

(30) Foreign Application Priority Data

Sep. 22, 2000  (WO) ................. PCT/BE00/00111
Sep. 21, 2001  (WO) .................. PCT/IB00/00163

(51) Int. Cl.
*A61K 9/48*     (2006.01)
*A61K 31/203*   (2006.01)
*A61K 47/44*    (2006.01)
*A61K 9/00*     (2006.01)
*A61K 47/10*    (2006.01)
*A61K 31/202*   (2006.01)
*A61K 9/107*    (2006.01)

(52) U.S. Cl.
CPC ............. *A61K 31/203* (2013.01); *A61K 9/1075* (2013.01); *A61K 9/4858* (2013.01); *A61K 9/4866* (2013.01); *A61K 47/44* (2013.01); *A61K 9/0014* (2013.01); *A61K 47/10* (2013.01); *A61K 31/202* (2013.01)
USPC ........................................................ 514/559

(58) Field of Classification Search
USPC ....................................................... 514/559
See application file for complete search history.

(56) References Cited

U.S. PATENT DOCUMENTS

| 4,464,394 A | 8/1984 | Bollag |
| 5,252,604 A | 10/1993 | Nagy et al. |
| 5,993,858 A | 11/1999 | Crimson et al. |
| 6,020,003 A | 2/2000 | Stroh et al. |
| 6,054,136 A | 4/2000 | Denis et al. |
| 6,248,363 B1 | 6/2001 | Patel et al. |
| 6,267,985 B1 | 7/2001 | Patel et al. |
| 6,294,192 B1 | 9/2001 | Patel et al. |
| 6,383,471 B1 | 5/2002 | Chen et al. |
| 6,593,292 B1 | 7/2003 | Rothbard et al. |
| 6,624,154 B1 | 9/2003 | Benoit et al. |
| 6,923,988 B2 | 8/2005 | Patel et al. |
| 2003/0077297 A1* | 4/2003 | Chen et al. ............ 424/400 |
| 2004/0009225 A1 | 1/2004 | Vanderbist et al. |

FOREIGN PATENT DOCUMENTS

| CA | 2423170 | 3/2002 |
| CA | 2762391 | 11/2010 |
| EP | 0 134 942 | 6/1986 |
| EP | 0 184 942 | 6/1986 |
| EP | 0184942 | 5/1987 |
| RU | 2400226 | 9/2010 |
| WO | WO 85/03434 | 8/1985 |
| WO | WO 99/44589 | 9/1999 |
| WO | WO 00/00179 | 1/2000 |
| WO | WO 00/25772 | 5/2000 |

OTHER PUBLICATIONS

Koga K, Kawashima S, Murakami M, "In vitro and in situ evidence for the contribution of Labrasol and Gelucire, 44/14 on transport of cephalexin and cefoperazone by rat intestine". Eur. J. Pharm. Biopharm. Nov. 2002 54(3): 311-8.
Koga, K., et al, "In vitro and in situ evidence for the contribution of Labrasol and Gelucire 44/14 on transport of cephalexin and cefoperazone by rat intestine", Eur. J. Pharm. Biopharm, Nov. 2002 54(3)311-8.
Internationai Journal of Pharmaceutics, 106:15-23 (1994), "Self-emulsifying drug delivery systems (SEDDS) with Polyglycolized Glycerides for improving in vitro dissolution and oral absorption of lipophilic drugs".
Nankervis, et al. "Intestinal lymphotic transport of three retinoids in the rat after oral administration: effect of lipophilicity and lipid vehicle", International Journal of Pharmaceutics, 130:57-64 (1996).
"Effect of Lipid Vehicle on the intestinal lymphatic transport of isotretinoin in the rat", International Journal of Pharmaceutics, 119:173-181 (1995).
Constantinides, "Lipid microemulsion for improving drug dissolution and oral absorption:Physical and Biopharmaceutical Aspects", Pharmaceutical Research, vol. 12 No. 11 (1995).
Gershank, "Self-dispersing lipid formulations for improving oral absorption of lipophilic drugs", Eur. Journal of Pharmaceuticals & Biopharm., 50:179-188 (2000).
Self-emulsifying Drug DeliverySystems (SEDDS) with Polyglycolized Glycerides for Improving in vitro Dissolution and Oral Absorption of Lipophilic Drugs, International Journal of Pharmaceutics, 106: 15-23 (1994).

(Continued)

*Primary Examiner* — Michael G Hartley
*Assistant Examiner* — Robert Cabral
(74) *Attorney, Agent, or Firm* — William E. Beaumont

(57) ABSTRACT

An oral pharmaceutical composition of isotretinoin containing at least two lipidic excipients, one of them being hydrophilic (i.e. having an HLB value superior or equal to 10), the other being an oily vehicle

12 Claims, 5 Drawing Sheets

(56) References Cited

OTHER PUBLICATIONS

Nankervis et al. Intestinal Lymphatic Transport of Three Retinoids in the Rat After Oral Administration; Effect of Lipophilicity and Lipid Vehicle, International Journal of Pharmaceutics, 130: 57-64 (1996).
Effect of Lipid Vehicle on the Intestinal Lymphatic Transport of Isotretinoin in the Rat, International Journal of Pharmaceutics, 119:173-181 (1995).

Constantinides, Lipid Microemulsions for Improving Drug Dissolution and Oral Absorption: Physical and Biopharmaceutical Aspects, Pharmaceutical Research, vol. 12, No. 11(1995).
Gershanik, Self-dispersing Lipid Formulation for Improving Oral Absorption of Lipophilic Drugs, European Journal of Pharmaceuticals and Biopharmaceuticals, 50:179-188 (2000).

* cited by examiner

PHARMACEUTICAL SEMI-SOLID COMPOSITION OF ISOTRETINOIN

This application is a continuation of application Ser. No. 11/892,363, filed on Aug. 22, 2007, which is a continuation of application No. 10/380,619, filed on Jul. 30, 2003, which is a §371 application of PCT/BE01/00163, filed on Sep. 21, 2001.

ABSTRACT OF THE DISCLOSURE

The present invention relates to an oral pharmaceutical composition of isotretinoin containing at least two excipients, one of them being hydrophilic (i.e. having an HLB value superior or equal to 10), the other being an oily vehicle.

THE PRIOR ART

Isotretinoin (13-cis retinoic acid or 13-cis vitamine A), its isomers and some of its analogs are widely known to have a therapeutical activity in the treatment of several severe skin disorders like cystic acne, hypertrophic lupus erythematosus, keratinization disorders. Some evidences have also been brought about the activity of isotretinoin in basal cell carcinoma and squamous cell carcinoma.

Unfortunately, isotretinoin is also a highly toxic drug. Indeed, although isotretinoin, which is a cis derivative, is known to be less toxic than all trans vitamine A derivatives, side effects resulting from its use such as headache, vomiting, irritation of mucosa and liver toxicity, occur frequently. Furthermore, isotretinoin is known to be highly teratogenic in both animals and humans.

In order to well understand the interest of this invention, it is important to briefly summarize the physico-chemical pharmacokinetic properties. Isotretinoin is a reddish-orange powder. It is decomposed in presence of light and atmospheric oxygen. Isotretinoin is very poorly soluble in water what mades its bioavailability quite low after an oral intake (25% in fasted conditions and 40% in fed conditions). The maximum concentration ($C_{max}$) is reached after 2-4 hours, while the ($C_{max}$) of the active metabolite, 4-oxo-isotretinoin is reached after 6 hours. The elimination half-life of isotretinoin is of 7 to 37 hours while the half life ($t_{1/2}$) of the active metabolite is of 11 to 50 hours. The steady-state concentrations of isotretinoin are reached after 1 week of treatment.

Very few publications and/or patents about the pharmaceutical formulation of isotretinoin are available. The drug is available on most markets under the form of a soft gelatine capsule containing a fatty liquid formulation of isotretinoin.

The U.S. Pat. No. 4,464,394 describing for the first time the therapeutical use of isotretinoin also describes briefly some possibilities of compositions including it. It involves the use of one antioxidant agent and of one carrier like lactose, starches or polyethyleneglycols.

The EP patent 0184942 describes more specific compositions of isotretinoin involving the use of one antioxidant, one chelating agent, one pharmaceutical carrier and one suspending agent. The composition obtained is stable during time.

The U.S. Pat. No. 4,545,977 relates to improved compositions of isotretinoin wherein taurine is associated with isotretinoin to reduce the side effects thereof.

The U.S. Pat. No. 5,716,928 describes a method for increasing bioavailability and for reducing inter and intra individual variability of an orally administered hydrophobic pharmaceutical compound, which comprises orally administering the pharmaceutical compound with an essential oil or essential oil component in an amount sufficient to provide greater bioavailability of the active ingredient.

The U.S. Pat. No. 6,028,054 relates to a method for increasing bioavailability of an orally administered hydrophobic pharmaceutical compound to human, which comprises orally administering the pharmaceutical compound concurrently with a bioenhancer comprising an inhibitor of e-cytochrome P450 3A enzyme or an inhibitor of P-glycoprotein mediated membrane transport.

The U.S. Pat. No. 5,993,858 describes a self microemulsifying excipient formulation for increasing the bioavailability of a drug which includes an emulsion including an oil or other lipid material, a surfactant and an hydrophilic co-surfactant.

What is not described is a composition of isotretinoin containing at least two lipid materials, one of them being hydrophilic. The said composition may be a suspension, emulsion or microemulsion.

BRIEF DESCRIPTION OF THE INVENTION

The advent of high throughput combinatorial chemistry and efficient receptor based in vitro activity screen has resulted in molecules with poor physicochemical (ex: dissolution) properties for absorption across the gastro-intestinal tract, like isotretinoin.

It is increasingly being recognized by the pharmaceutical industry that for these molecules drug delivery systems play an important role for improving oral bioavailability.

Although the process of passive diffusion is responsible for absorption of non ionized lipophilic molecules via the transcellular pathway, specialized absorption mechanisms, first-pass metabolisms and efflux systems at the gastrointestinal wall appear to play a major role for lack of absorption and poor bioavailability for some molecules.

Isotretinoin is characterized by a low absolute bioavailability and a high inter and intra individual variability. Isotretinoin also presents a wide range of side effects among which some are severe (ocular, skin anemia, hepatic, . . . ). It is consequently of a particular interest to dispose of a reliable, stable and highly bioavailable formulation of isotretinoin.

Several possibilities are available to the formulator to increase the bioavailability of active ingredients (Table A).

TABLE A

| | |
|---|---|
| I. | Use of salts, polymorphs. Precursors of the active molecule (=prodrugs) |
| II. | Reduction of the particles' size of the active principle and of the excipients used (by trituration, grinding, micronization, precipitation controlled by solvent, temperature or ultrasonics). |
| III. | Solid dispersions: Eutectic mixes Solid solutions Vitreous solutions |
| IV. | Recrystallization in an aqueous solution of a surfactant |
| V. | Modification of the microenvironment: Hydrophilization pH (acidification) |
| VI. | Incorporation of the active principle to lipidic systems |

It has been found that a semi-solid dosage form containing isotretinoin was advantageous for obtaining a good bioavailability of the isotretinoin. A semi-solid dosage form containing isotretinoin is a form in which isotretoin is mixed with suitable melted excipients. The molten mix is then filled for example into hard gelatine capsules or other pharmaceutically acceptable capsules. At ambient temperature (temperature for example of less than 20° C.), the content of the capsule is solid while at temperature higher than 20° C. (for example at temperature greater or equal to 30° C., advantageously greater or equal to 35° C., preferably substantially at body temperature +/−37° C.), it is liquid or semi-solid (paste). The isotretinoin may be solubilized in the mix of excipients or partially solubilized. The active ingredient may also be formulated as a suspension, emulsion or microemulsion. Various lipidic excipients are available to the formulator to obtain a semi-solid formulation. Excipients compatible with hard gelatin capsule shells are: lipophilic liquid vehicles (refined speciality oils, medium-chain triglycerides and related esters), semi-solid lipophilic vehicles, solubilizing agents, emulsifying agents and absorption enhancers. The classification of fatty excipients is based on the hydrophilicity or lipophilicity of the excipients, characterized by the hydrophilic/lipophilic balance value (HLB). Examples of lipophilic excipients are vegetable oils (peanut oil, olive oil, soyabean oil, . . . ), fatty acids (stearic acid, palmitic acid, . . . ), fatty alcohols, . . . Examples of hydrophilic excipients are polyethyleneglycol (PEG) with a molecular weight superior to 3,000. Examples of amphiphilic (=presenting lipophilic and hydrophilic properties) excipients are Poloxamers, Lecithin, PEG esters (Gelucire®), . . . .

The advantages of the semi-solid formulations of the invention are multiple for isotretinoin: protection of the active ingredient from air and humidity, possibility of increasing the dissolution rate of the molecule and hence of the bioavailability, diminution of the risk of contamination of the operator, diminution of the risk of cross contamination, no possibility of demixing under the effect of vibrational mixing during manufacturing process, facility of the production process. The choice of the nature of the formulation of course influenced the stability of the pharmaceutical form and the bioavailability of the isotretoin contained in it. Generally, a maximum bioavailability is achieved by preparing and keeping the drug in the amorphous/solubilized state in a solid dispersion or in a lipid-based formulation. For these systems, the barrier we are avoiding is the compound <<washing-out>> of solution to a large extent into a insoluble crystalline form during the dissolution/release step in vivo.

These systems may consist of suspension, emulsion, microemulsion, self-emulsifying drug delivery systems (SEDDS®) or self-emulsifying microemulsion drug delivery system (SMEDDS®).

Microemulsions have the added advantage over suspensions such as emulsions and dispersions since thermodynamically they are more stable, that they can be manufactured with little energy input and have generally a longer shelf-life. Nevertheless, a microemulsion formulation is not a guarantee of higher bioavailability in comparison to suspension a described hereafter.

The formation of oil-in-water (O/W) and water-in-oil (W/O) microemulsions usually involves a combination of 3-5 basic compounds i.e. oil, surfactant, cosurfactant, water and electrolytes. The challenge is to select for a particular application oil(s) and surfactant(s) that are acceptable from a toxicological perspective and that allow to obtain a high bioavailability of the drug, i.e isotretoin.

The assessment of the quality of semi-solid lipid based formulations is quite difficult since the in vitro dissolution test is of little help. Indeed, the in vitro/in vivo correlation between dissolution and bioavailability is very poor for this kind of formulations. Other analytical tools are available to the formulator to try to predict the in vivo bioavailability of isotretinoin from various formulations like CACO-2 cells model, the assessment of the percentage of drug dissolved in the formulation, differential scanning calorimetry, microscopy, . . . .

Nevertheless, none of them present a guarantee of in vitro/in vivo correlation and ultimately only pharmacokinetic studies on human subjects are reliable to assess the bioavailabiltiy of the drug.

DESCRIPTION OF THE INVENTION AND PREFERRED EMBODIMENTS

The pharmaceutical composition of the invention is an oral semi-solid pharmaceutical composition of isotretinoin containing two lipidic excipients, one of them being hydrophilic i.e. having a HLB value of at least 10, for example equal to 10, but preferably greater than 10, such as greater or equal to 12, for example comprised between 12 and 14, and the other being an oily vehicle.

The pharmaceutical composition of the invention contains advantageously at least one hydrophilic excipient with a HLB value of at least 10 selected from the group consisting of glyceroyl macrogolglycerides, polyethyleneglycol derivatives, and mixtures thereof. Preferably, the pharmaceutical composition contains from 20 to 80% by weight of hydrophilic excipient with a HLB value of at least 10 selected from the group consisting of glyceroyl macrogolglycerides, polyethyleneglycol derivatives, and mixtures thereof.

The oily vehicle is selected from the group consisting of vegetable oils, medium chain triglycerides, fatty acid esters, amphiphilic oil, glycerol oleate derivative, and mixtures thereof. For example, the composition contains from 5 to 70% by weight of an oily vehicle selected from the group consisting of vegetable oils, medium chain triglycerides, fatty acid esters, amphiphilic oil, glycerol oleate derivative, and mixtures thereof.

According to another detail of preferred pharmaceutical compositions of the invention, the composition further contains at least one surfactant, preferably selected from the group consisting of sorbitan fatty acid esters, polysorbate derivatives, polyoxyethylene sorbitan fatty acid esters, sodium laurylsulphate, derivatives of lecithine, propylene glycol esters, fatty acid esters of propylene glycol, fatty acid esters of glycerol, polyethylene glycol, and mixtures thereof. For example, the composition contains from 1 to 10% by weight of at least one surfactant.

Furthermore, the pharmaceutical formulation of the invention contains advantageously at least one disintegrant, preferably selected from the group consisting of povidone derivative, sodium croscarmellose and mixtures thereof.

The pharmaceutical composition of the invention may contain one or more surfactants and/or one or more disintegrants, but contains preferably one or more compounds acting as surfactants and one or more compounds acting as disintegrants.

The invention relates also to a pharmaceutical acceptable capsule containing at least one semi-solid composition of the invention, for example at least one composition of the invention as disclosed hereabove. The capsule is for example selected from the group consisting of hard gelatine capsules, soft gelatine capsules, hypromellose capsules, starch capsules.

DESCRIPTION OF EXAMPLES

The present invention relates thus to a semi-solid formulation of isotretinoin containing at least 2 lipidic excipients, one of them being an hydrophilic excipient (having a high HLB value namely >10) and the other an oily excipient. The molten mix of these two excipients allows to totally or partially (depending on the ratio between excipients) dissolve isotretinoin. Different kinds of formulations (SEDDS® or suspensions) of isotretinoin have been formulated. For suspensions, it was possible to dissolve a high fraction of isotretinoin in the mix of excipients and even the whole quantity of the active ingredient if the manufacturing conditions (high temperature and long time of mixing) and the formulations were optimized. Excipients particluarly suitable for the dissolution of isotretinoin were lauroyl Macrogol-32 glycerides (Gelucire® 44/14, Gattefossé) and Stearoyl Macrogol-32 glycerides (Gelucire® 50/13, Gattefossé). When those hydrophilic components are melted together with an oily vehicle, it allows to obtain very stable suspensions of isotretinoin in which an important part of the active ingredient is dissolved. A surfactant may also be added to the formulation to still improve the physical stability of the suspension.

SEDDS® formulations of isotretinoin are also stable and may give an improved bioavailability of the drug.

Figure 1:
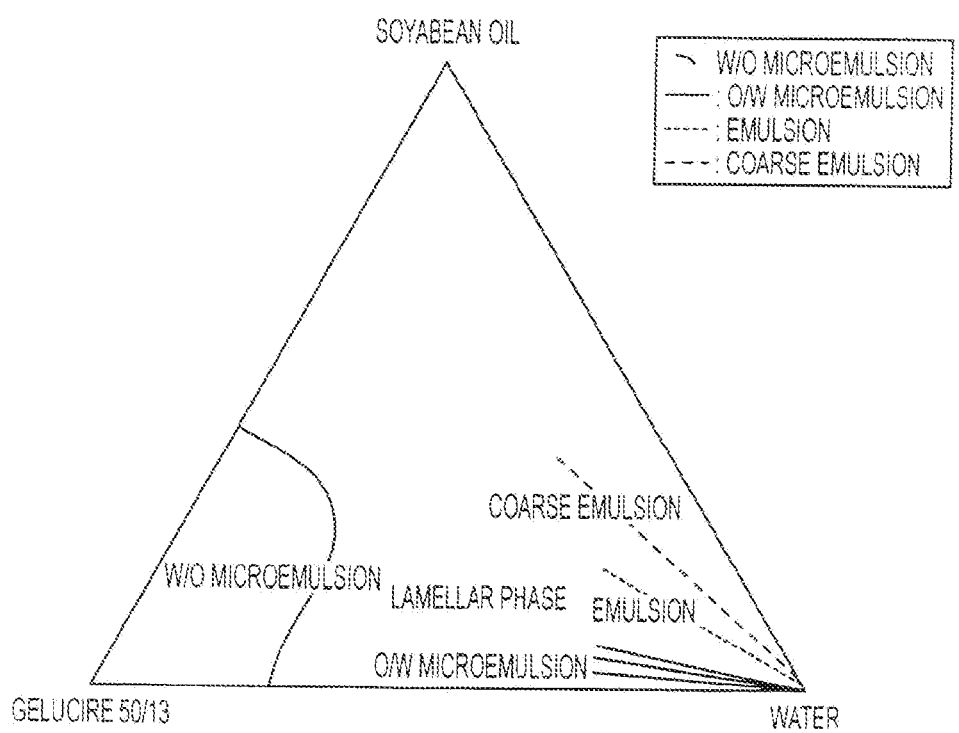
FIG. 1 is a ternary diagram of a formulation containing only Gelucire® 50/13 and soyabean oil, the third component being water.

Ternary diagrams allow to observe different areas corresponding to different physical states namely coarse emulsion, true emulsion, lamellar solution or micellar solution when the ratio between excipients changes. The behaviour of the formulation in presence of water changes when the ratio changes. One example of this ternary diagram is given in FIG. 1 for a formulation of isotretinoin containing Gelucire® 50/13 and soyabean oil.

EXAMPLES

Example 1

Effect of Different Lipophilic Compounds

The effect of different lipophilic excipients was evaluated in the form of semi-solid capsules. The semi-solid capsules were made by addition of the active substance at the pre-melted lipophilic compounds followed by the filling of the liquid into hard gelatin capsule.

The active substance was incorporated into formulations, listed in table I, consisting of glyceroyl macrogolglyceride associated with soyabean oil or derivative, medium chain triglyceride.

TABLE I

| | Formulations n° | | | | |
|---|---|---|---|---|---|
| | 1 | 2 | 3 | 4 | 5 |
| | | | (mg) | | |
| Isotretinoin | 20 | 20 | 20 | 20 | 20 |
| Labrafil ® M1944 CS | 132 | | | | |
| Gélucire ® 50/02 | 198 | 93 | | | |
| Gélucire ® 44/14 | | 217 | | | |
| Gélucire ® 50/13 | | | 76 | 60 | 60 |
| Soya bean oil | | | 304 | 320 | |
| Mygliol ® | | | | | 320 |

The use of stearoyl macroglyceride (Gélucire® 50/13, Gattefosse) and soyabean oil allows to obtain a formulation with a dissolution profile similar to the reference (Roaccutane® 20 mg, Roche).

The formulation with labrafil or Gelucire® 50/02 are too lipophilic to give a good dissolution in water.

In general, the use of an oily excipient can improve the absorption of lipophilic drug by increasing the solubility of the drug in the lipidic phase, but the release of the active ingredient from the formulation can be slowed down due to the high affinity of the drug for the oily phase.

The use of dispersed systems (emulsions or suspensions) instead of only lipophilic or hydrophilic vehicles, improves the absorption of the drug as well as increasing a larger contact surface.

Concerning the Gelucire®, the process of drug release varies according to the HLB of the excipient. Gelucire® with high HLB values were found to be the most favorable for a rapid release of the drug (by diffusion and erosion).

The drug release profiles of the formulations 1 to 5 were evaluated in phosphate buffer pH 7.5 with laurylsulfate and pancreatin. The percent of isotretinoin released after 4 hours is given in the following table II.

TABLE II

| percent of isotretinoin released after 4 hours | | | | | |
|---|---|---|---|---|---|
| Formulations n° | 1 | 2 | 3 | 4 | 5 |
| % released | 20.1 | 69.1 | 46.0 | 60.3 | 78.1 |

The percent of isotretinoin released from the reference (Roaccutane® 20 mg) after 4 hours is 55.37%

Example 2

Influence of the Ratio Oily Vehicle/Surfactive Agent on the Dissolution and Absorption of the Formulation The study of the ratio oily vehicle/surfactive agent with the construction of a ternary diagram gives information on the dissolution profile of the formulation in water.

Stearoyl macrogolglyceride (Gelucire® 50/13) known as a drug solubilizer and emulsifying agent of different drugs (in SMEDDS® or SEDDS®) was tested in association with soyabean oil.

This component has the ability to solubilize a great part of isotretinoin in the formulation.

This is listed in table III

TABLE III

|  | Formulations n° | | | | | |
|---|---|---|---|---|---|---|
|  | 1 | 2 | 3 | 4 | 5 | 6 |
|  | | | | (mg) | | |
| Isotretinoin | 20 | 10 | 10 | 20 | 20 | 20 |
| Soyabean oil | 270 | 135 | 40 | 152 | 57 | 133 |
| Gelucire ® 50/13 | 84 | 42 | 200 | 228 | 323 | 247 |
| Filling weight | 374 | 187 | 260 | 400 | 400 | 400 |
| Ratio oil/Gelucire ® 50/13 | 3.2 | 3.2 | 0.2 | 0.67 | 0.17 | 0.54 |

In the presence of water, the behaviour of these formulations are different
 formulations 1 and 2: formation of coarse emulsion with large droplet sizes
 formulations 3 and 5: formation of micellar phase or microemulsion
 formulations 4 and 6: formation of emulsion with homogeneous droplet size The percentage of isotretinoin released increases generally with the percentage of Gelucire® in the formulation (increased solubility of the active in this vehicle). For the formulation 1 (ratio oil/Gelucire® 50/13=3.2) 54.9% released after 4 hours and for the formulation 3 (ratio oil/Gelucire® 50/13:0.2), 91.2% released after 4 hours.

Dissolution Test

For poorly soluble molecules, the prediction power of the in vitro dissolution test is weak since the in vitro/in vivo correlation is known to be poor. Nevertheless, an optimized dissolution test (using enzymes and surfactant) is of some help to assess the rate of release of the drug from the lipidic composition. It must be noted that the conditions of the dissolution (dissolution medium, speed of the paddles, temperature, . . . ) test influence dramatically the results of the test and should consequently be standardized to allow comparison between various formulations.

Figure 2:
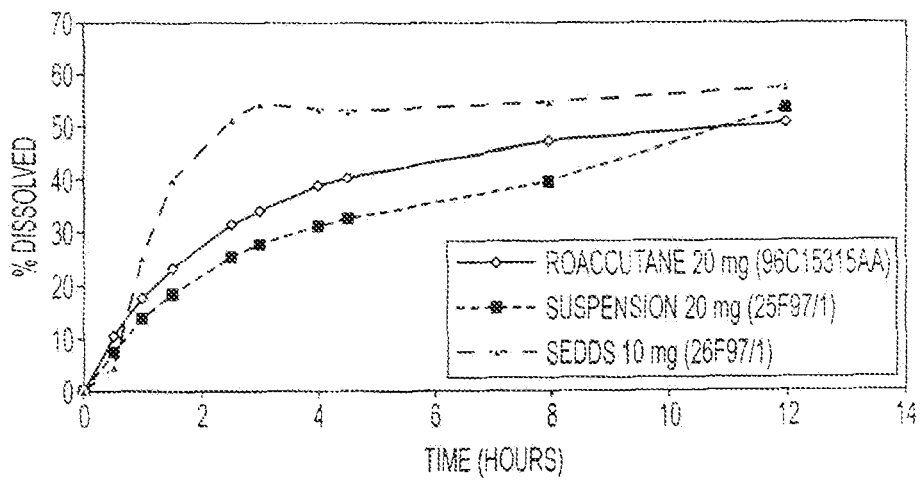
FIG. 2 shows the dissolution rate of a reference product (Roaccutane®—20 mg active agent), of a suspension containing 20 mg Isotretoin and of an emulsion SEDDS® containing 10 mg Isotretoin.

The conditions of the solution test used for assessing the dissolution of isotretinoin were the following:
 paddle apparatus
 150 rpm
 37° C.
 buffer pH 7.5 with laurylsulfate 2.5% and pancreatin 1 g/L FIG. 2 shows the dissolution rate of a reference product (Roaccutane® —20mg active agent), of a suspension containing 20 mg Isotretoin and of an emulsion SEDDS® containing 10 mg Isotretoin (formulation given hereinbelow).

As the information brought by the dissolution test is poor in term of correlation with in vivo bioavailability, it is of interest to dispose of other means to predict the in vivo bioavailability.

The caco-2 cell culture system can be used for determining permeability of compounds (especially for poorly soluble compounds). The caco-2 cell model allows to measure the transport of drug from the apical to the serosal side as well as from the serosal to the apical side. This allows to determine if an efflux system is operational.

The caco-2 cells model is interesting because:
 The cells used are from human origin (contrary to the models using segments of animal's guts). They are coming from an adenocarcinoma of the human colon but spontaneously differentiate into small intestine's epithelail cells. When put in culture, they form a monolayer of polarized cells expressing several enzymatic systems.
 It offers a better prediction of the human intestine absorption than the animals models
 The reproducibility of the test is relatively high
 It allows to take samples from both apical and basolateral sides Caco-2 cells experiments have been performed with one SEDDS® and one suspension isotretinoin formulations.

Results

It was first proven that neither the active ingredient nor the excipient used in the formulations were toxic for the cells. It was also proven that the integrity of the membranes of the cells was maintained during the whole experience.

Methodology:

The formulations tested are put in solution in 250 ml of BME. Taurocholate (10 mM) was added to the solutions to better mimate the in physiological conditions. The different solutions so prepared are put in contact with Caco-2 cells at the apical or basolateral side. The cells culture inserts) are incubated for 3 hours at 37° C. and samples of 100 µl are taken every hours The formulations tested were the following:
 Formulation SEDDS® (batch number 26F97/1):
Isotretinoin: 10 mg
Gelucire® 50/13: 134 mg
Phospholipon 90®: 11 mg
Tween 80®: 71 mg
IPP®: 24 mg
Pro capsula una
 Formulation suspension (batch number 25F97/1)
Isotretinoin: 20 mg
Gelucire® 50/13: 83.7 mg
Soyabean oil: 270 mg
Procapsula una Results Passage of formulations from apical side→basolateral side

| Time minutes | SEDDS ® (26F97/1) | Suspension (25F97/1) | SEDDS ® + TC | Suspension + TC | control |
|---|---|---|---|---|---|
| 60 | 0.7721 | 0.6708 | 0.7019 | 0.6469 | 0.0718 |
| 120 | 2.4096 | 0.8749 | 1.4347 | 0.9513 | 0.1836 |
| 180 | 2.6226 | 1.1311 | 3.2419 | 1.5073 | 0.6156 |

Passage of formulations from basolateral side→apical side

| Time minute | SEDDS ® (26F97/1) | Suspension (25F97/1) | SEDDS ® + TC | Suspension + TC | control |
|---|---|---|---|---|---|
| 60 | 2.0496 | 0.3948 | 8.1291 | 0.8713 | 0.0650 |
| 120 | 3.0844 | 0.9068 | 8.3496 | 1.8460 | 0.1131 |
| 180 | 4.3653 | 1.0763 | 9.7110 | 2.0779 | 0.1481 |

The results demonstrate that the passage of isotretinoin is superior for the SEDDS® formulation than for the suspension formulation. In order to confirm these results, a comparative pharmacokinetics study has been performed.

PK Studies

The bioavailability of SEDDS® (26F97/1) and suspension (25F97/1) isotretinoin formulations has been assessed and compared to the bioavailability of the reference (Roaccutane® 20 mg, Hoffman LaRoche) on six healthy volunteers in a single dose, three way, cross-over pharmacokinetic study). The drug was taken with food (standardized breakfast). The plasma concentration of isotretinoin and its active metabolite 4-oxo-isotretinoin were quantified using a fully validated LC/MS/MS method.

Figure 3:
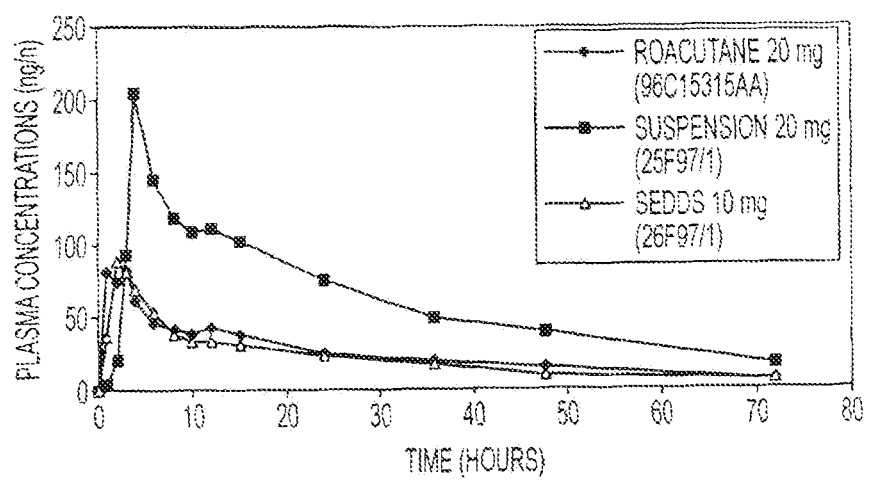
FIG. 3 shows an In vivo comparative pharmacokinetic profile of isotretinoin.

The FIG. 3 described the mean pharmacokinetic profile obtained for each formulation.

The following table gives the value of the main pharmacokinetics parameters obtained for each formulation of isotretinoin.

| Formulations | $AUC_{72h}$ (ng·h/ml) | $C_{max}$ (ng/ml) | $T_{max}$ (h) |
|---|---|---|---|
| Roaccutane ® 20 mg (96C15315AA) | 1747.89 | 116.63 | 1.83 |
| Suspension 20 mg (25F97/1) | 4308.72 | 230.96 | 5.67 |
| SEDDS ® 10 mg (26F97/1) | 1494.64 | 98.36 | 3.00 |

It appears that both the SEDDS® and the suspension formulation are able to significantly increase the bioavailability of isotretinoin in comparison to the marketed reference. Indeed the ratio between $AUC_{72h}$ of the supension 20 mg and Roaccutane® 20 mg is of 2.47. The SEDDS® 10 mg present an $AUC_{72h}$ similar to this of Roaccutane® 20 mg what means an approximately 2-fold increase of bioavailability (ratio $AUC_{72h}$ SEDDS® 10 mg/$AUC_{72h}$ Roaccutane® 20 mg=0.86). Furthermore, the suspension and SEDDS® formulations both presented a lower intraindividual variability of the bioavailability as demonstrated by the values of relative standard deviations (rsd) which are of 36.0%, 22.72% and 28.18% for Roaccutane® 20 mg, suspension 20 mg and SEDDS® 10 mg respectively.

Nevertheless, the results obtained in vivo are not correlated with the results obtained on caco-2 cells since on this model the permeability of the SEDDS® formulation was much higher than the permeability of the suspension formulation while in vivo the suspension formulation gives the best results.

Figure 4:
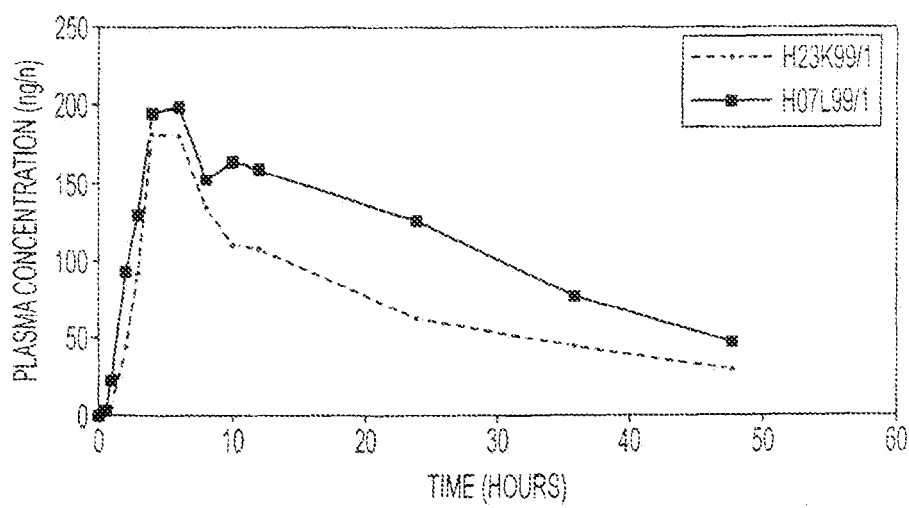
FIG. 4 gives the comparative pharmacokinetic profile of different formulations for isotretinoin, FIG. 5 gives the comparative pharmacokinetic profile of different formulations for 4-oxo-isotretinoin, the active metabolite of isotretinoin and FIGS. 6 and 7 describe the mean pharmacokinetic profile of isotretinoin and 4-oxoisotretinoin for two formulations.
Figure 5:
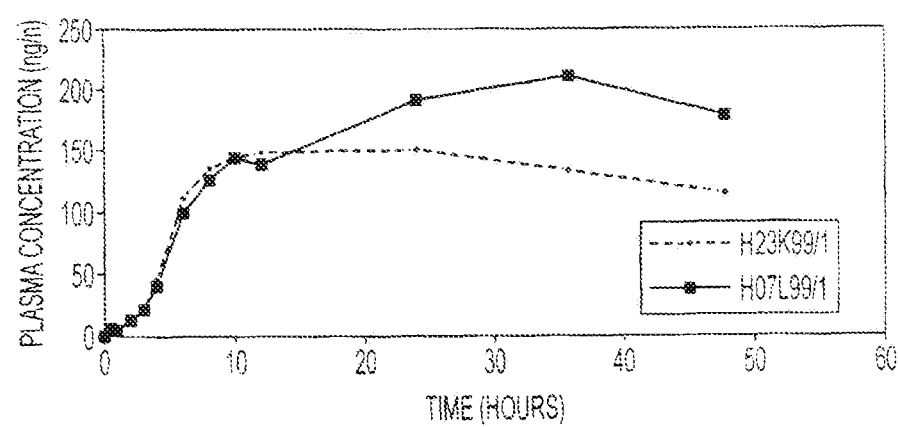

A second pharmacokinetic study was performed on completely different formulations (6 subjects, 2-way, fed, crossover study). Those were formulations of isotretinoin under the form of a suspension in which the ratio between Gelucire® 50/13 and soyabean oil was very different that the previous formulation of suspension The two formulations tested were the following:

F1: suspension without surfactant (batch number H23K99/1)
Isotretinoin: 20 mg
Gelucire® 50/13: 247 mg
Soyabean oil: 133 mg F2: suspension with surfactant (batch number H07L99/1)
Isotretinoin: 20 mg
Gelucire® 50/13: 240 mg
Soyabean oil: 130 mg
Span 80®: 20 mg The FIG. 4 gives the comparative pharmacokinetic profile of each formulation for isotretinoin The FIG. 5 gives the comparative pharmacokinetic profile of each formulation for 4-oxo-isotretinoin, the active metabolite of isotretinoin.

In order to confirm the first bioavailability data obtained with the present invention, a larger pharmacokinetic study has been performed.

The bioavailability of a capsule of isotretinoin 16 mg (see the formulation herebelow) from the present invention has been assessed and compared to the bioavailability of the reference (ROACCUTANE® 20 mg capsule, Roche) on 24 healthy subjects.

This study (SMB-ISO-SD011) was a single dose, two treatment, two period, two sequence, randomised, crossover and with at least 18 days wash-out between the two periods.

The subjects were healthy caucasian volunteers of both sexes (non-pregnant, non-breast-feeding), aged 18 to 50 years, non smokers or smoking less than 10 cigarettes per day.

The drugs was taken with food (a standardized breakfast).

Blood samples were collected according to the following sampling schedule: pre-dose and 1 h, 2 h, 3 h, 4 h, 5 h, 6 h, 7 h, 8 h, 10 h, 12 h, 14 h, 24 h, 36 h, 48 h, 72 h, 96 h, 120 h, 168 h and 216 hours post-dose.

The plasma concentration of isotretinoin and its active metabolite 4-oxo-isotretinoin were quantified using a fully validated LC/MS/MS method. The continuous variables were evaluated according to an univariate ANOVA, based on log-transformed data. The Wilcoxon non-parametric ANOVA were used where appropriate. Bioequivalence was evaluated using the Shuirman two one-sided t-test (90% Cl) and the westlake single sided confidence interval (95% CL)

Figure 6:
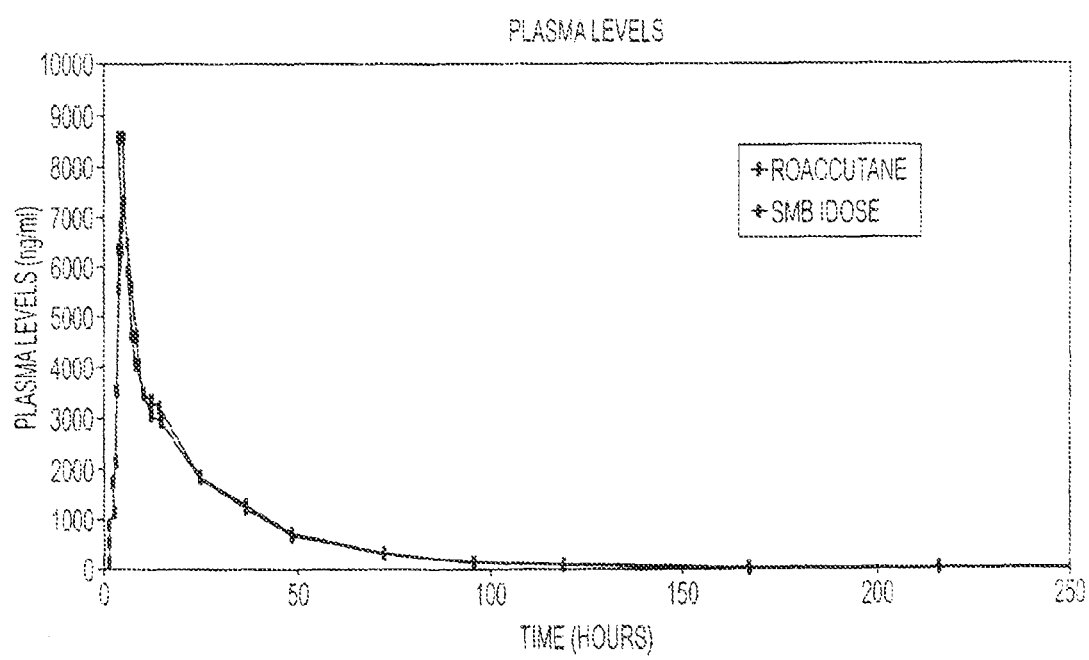
Figure 7:
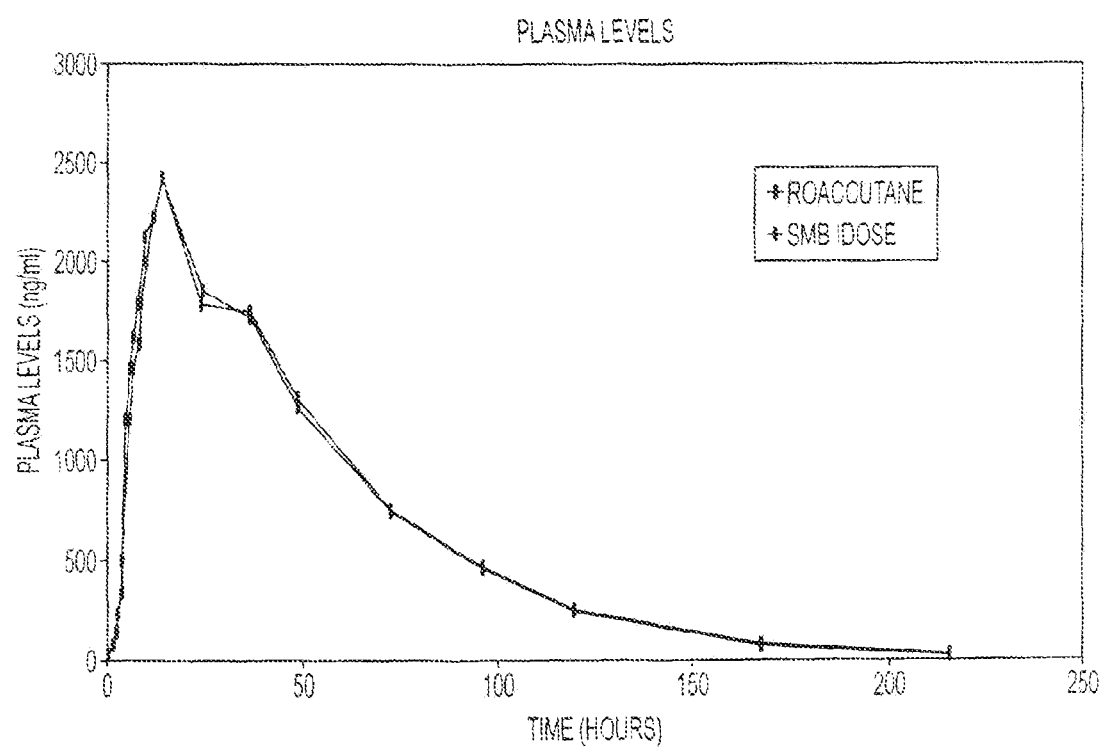

The FIGS. 6 and 7 describe the mean pharmacokinetic profile of isotretinoin and 4-oxoisotretinoin for the two formulations (n=24 subjects) while the tables herebelow give the comparative main pharmacokinetic parameters.

Formulation of isotretinoin 16 mg (mg/capsule)

| | |
|---|---|
| isotretinoin | 16 |
| stearoyl macrogol glycerides (Gelurire 50/13 ®) | 192 |
| soya bean oil refined | 104 |
| sorbitane oleate (Span 80 ®) | 16 |

As seen, the dose of 16 mg of the formulation corresponding to the present invention gives a bioavailability similar to 20 mg of the marketed formulation, what is the evidence of the supra-bioavailability of the formulation corresponding to the present invention.

The tables hereinbelow gives the value of the main pharmacokinetics results and statistical analysis obtained for each formulation of isotretinoin and 4-oxoisotretinoin.

This study demonstrated that ROACCUTANE® 20 mg and isotretinoin 16 mg x are bioequivalent after a single oral dose administration of each product in fed conditions. Indeed, the primary parameters AUC ($AUC_\infty$ and $AUC_{216h}$) were within the predetermined confidence interval.

This study demonstrated also that Isotretinoin 16 mg has a safety profile comparable with that described in the literature for other isotretinoin preparations and similar to this of ROACCUTANE® 20 mg.

Pharmacokinetic results and statistical analysis of comparative study in 24 volunteers for isotretinoin (log-transformed data)

| | Results | | Bioequivalence tests | |
|---|---|---|---|---|
| | | | Shuirman | Westlake |
| Parameter | ROACCUTANE ® 20 mg | Isotretinoin 16 mg | 90% CI Range | 95% CL |
| $AUC_\infty$ | 5657.09 (ng · h/ml) | 5696.92 (ng · h/ml) | 92-123 | 19.07 |
| ± SD | ± 2682.98 | ± 1938.89 | | |
| ± RSD | ± 47.42 | ± 34.03 | | |
| $AUC_{216h}$ | 5601.36 (ng · h/ml) | 5664.39 (ng · h/ml) | 92-124 | 19.51 |
| ± SD | ± 2670.85 | ± 1953.52 | | |
| ± RSD | ± 47.68 | ± 34.48 | | |
| $C_{max}$ | 386.68 (ng/ml) | 441.79 (ng/ml) | 103-140 | 28.81 |
| ± SD | ± 218.21 | ± 197.43 | | |
| ± RSD | ± 56.43 | ± 44.68 | | |
| $T_{max}$ | 4.92 (h) | 4.50 (h) | / | / |
| ± SD | ± 2.22 | ± 0.66 | | |
| ± RSD | ± 45.24 | ± 14.65 | | |

Pharmacokinetic results and statistical analysis of comparative study in 24 volunteers for 4-oxoisotretinoin (log-transformed data)

| | Results | | Bioequivalence tests | |
|---|---|---|---|---|
| | | | Shuirman | Westlake |
| Parameter | ROACCUTANE ® 20 mg | Isotretinoin 16 mg | 90% CI Range | 95% CL |
| $AUC_\infty$ | 5750.36 (ng · h/ml) | 5769.04 (ng · h/ml) | 92-124 | 19.65 |
| ± SD | ± 2717.38 | ± 2161.97 | | |
| ± RSD | ± 47.26 | ± 37.48 | | |
| $AUC_{216h}$ | 5638.32 (ng · h/ml) | 5712.21 (ng · h/ml) | 92-125 | 20.46 |
| ± SD | ± 2704.73 | ± 2126.61 | | |
| ± RSD | ± 47.80 | ± 37.23 | | |
| $C_{max}$ | 111.52 (ng/ml) | 115.15 (ng/ml) | 94-125 | 20.18 |
| ± SD | ± 69.62 | ± 66.25 | | |
| ± RSD | ± 62.43 | ± 57.53 | | |
| $T_{max}$ | 17.83 (h) | 16.33 (h) | / | / |
| ± SD | ± 10.60 | ± 10.11 | | |
| ± RSD | ± 59.43 | ± 61.88 | | |

What we claim is:

1. An oral pharmaceutical composition in the form of a capsule, wherein the capsule is filled with a composition consisting essentially of a semisolid paste of isotretinoin in a mixture of oil and a glycerol macrogolglyceride of HLB of at least 10, said composition exhibiting a dissolution of at least 40% within 4 hours as measured using USP paddle apparatus at 150 rpm in an aqueous dissolution medium constituted by buffer of pH 7.5, sodium lauryl sulfate 2.5% and pancreatin 1 g/L at 37° C.

2. The oral pharmaceutical composition of claim 1, wherein the composition exhibits an isotretinoin release rate of at least 60% within 4 hours.

3. The oral pharmaceutical composition of claim 1, wherein isotretinoin comprises between 1% to 25% w/w of the composition, the oil comprises between 20% to 80% w/w of the composition and the macrogolglyceride comprises between 5% to 70% w/w of the composition.

4. The oral pharmaceutical composition of claim 1, wherein the oil excipient is selected from the group consisting of vegetable oils, medium chain triglycerides, fatty acid esters, glycerol oleate and mixtures thereof.

5. The oral pharmaceutical composition of claim 1, wherein the glycerol macrogolglyceride excipient has a HLB value of at least 12.

6. The oral pharmaceutical composition of claim 1, wherein the glycerol macrogolglyceride excipient has a HLB value of at least 13.

7. The oral pharmaceutical composition of claim 1, wherein the composition is as semi-solid suspension.

8. The oral pharmaceutical composition of claim 1, which further comprises at least one surfactant.

9. The oral pharmaceutical composition of claim 8, wherein the surfactant is selected from the group consisting of sorbitan fatty acid esters, polysorbate compounds, polyoxyethylene sorbitan fatty acids esters, sodium lauryl sulphate compounds of lecithin, propylene glycol esters, fatty acid esters of propylene glycol, fatty acid esters of glycerol, and mixtures thereof.

10. The oral pharmaceutical composition of claim 8, wherein the surfactant comprises between 1% to 10% w/w of the composition.

11. The oral pharmaceutical composition of claim 1, which further comprises at least one disintegrant.

12. The oral pharmaceutical composition of claim 11, wherein the disintegrant is selected from the group consisting of crospovidone, sodium croscarmellose, and mixtures thereof.

* * * * *